United States Patent
Jung et al.

(10) Patent No.: US 10,000,785 B2
(45) Date of Patent: Jun. 19, 2018

(54) COMPOSITION OF REDOX-REAGENTS FOR ELECTROCHEMICAL BIOSENSOR AND BIOSENSOR COMPRISING THE SAME

(71) Applicants: Sung-kwon Jung, Wonju-si (KR); Moon Hwan Kim, Seoul (KR); Myeong-Ho Lee, Seoul (KR); Ung-Ki Lee, Seoul (KR); Yeon-Ho Jung, Namyangju-si (KR); Han-Be Park, Wonju-si (KR); Hakhyun Nam, Seoul (KR); Geun Sig Cha, Seoul (KR)

(72) Inventors: Sung-kwon Jung, Wonju-si (KR); Moon Hwan Kim, Seoul (KR); Myeong-Ho Lee, Seoul (KR); Ung-Ki Lee, Seoul (KR); Yeon-Ho Jung, Namyangju-si (KR); Han-Be Park, Wonju-si (KR); Hakhyun Nam, Seoul (KR); Geun Sig Cha, Seoul (KR)

(73) Assignee: I-SENS, INC., Seoul (KR)

( * ) Notice: Subject to any disclaimer, the term of this patent is extended or adjusted under 35 U.S.C. 154(b) by 80 days.

(21) Appl. No.: 13/639,264

(22) PCT Filed: Sep. 25, 2012

(86) PCT No.: PCT/KR2012/007711
§ 371 (c)(1),
(2) Date: Nov. 12, 2012

(87) PCT Pub. No.: WO2013/048087
PCT Pub. Date: Apr. 4, 2013

(65) Prior Publication Data
US 2013/0081958 A1    Apr. 4, 2013

(30) Foreign Application Priority Data

Sep. 30, 2011    (KR) .................. 10-2011-0100018
Jan. 31, 2012    (KR) .................. 10-2012-0009668

(51) Int. Cl.
*C12Q 1/00*    (2006.01)
*G01N 27/327*    (2006.01)

(52) U.S. Cl.
CPC ............ *C12Q 1/006* (2013.01); *C12Q 1/004* (2013.01); *G01N 27/3272* (2013.01)

(58) Field of Classification Search
CPC ........... C12Q 1/00–1/001; C12Q 1/004; C12Q 1/006; C12Q 1/54; G01N 27/3272
(Continued)

(56) References Cited

U.S. PATENT DOCUMENTS 5,120,420 A    6/1992    Nankai et al.
5,126,247 A    6/1992    Palmer et al.
(Continued)

FOREIGN PATENT DOCUMENTS

CN    1573324 A    3/2004
CN    101970680 A    2/2011
(Continued)

OTHER PUBLICATIONS

Fletcher et al., Microbos, 80 (324), 181-188.*
(Continued)

*Primary Examiner* — Gurpreet Kaur
(74) *Attorney, Agent, or Firm* — Lucas & Mercanti, LLP

(57) ABSTRACT

A composition of redox-reagent containing metal-containing complex and thionine or its derivative as electron transfer mediator for use in an electrochemical biosensor, and a biosensor containing the same are provided. With the increase in reaction rate between redox enzyme-thionine (or its derivative)-metal-containing complex in the composition of redox-reagent containing metal-containing complex and thionine or its derivative, glucose detection efficiency markedly increases, and the composition is hardly influenced from high humidity and interfering substances. Accordingly,
(Continued)

the composition of redox-reagent is useful in fabricating an electrochemical biosensor for detecting glucose in blood.

19 Claims, 9 Drawing Sheets

(58) Field of Classification Search
USPC .... 204/403.01–403.15; 205/777.5, 778, 792; 600/345–348; 435/4–40.52
See application file for complete search history.

(56) References Cited

U.S. PATENT DOCUMENTS

| | | | |
|---|---|---|---|
| 5,460,819 A * | 10/1995 | Gallop et al. | 514/292 |
| 7,550,290 B2 * | 6/2009 | Yamamoto | 435/287.8 |
| 2002/0027072 A1 * | 3/2002 | Cui | C12Q 1/004 204/403.1 |
| 2005/0000808 A1 | 1/2005 | Cui et al. | |
| 2006/0175205 A1 * | 8/2006 | Cui et al. | 205/777.5 |
| 2007/0056852 A1 * | 3/2007 | Kubo et al. | 204/403.14 |
| 2007/0131546 A1 * | 6/2007 | Nomoto et al. | 204/403.01 |
| 2007/0235346 A1 * | 10/2007 | Popovich et al. | 205/777.5 |
| 2007/0295616 A1 | 12/2007 | Harding et al. | |
| 2008/0277292 A1 * | 11/2008 | Heller et al. | 205/777.5 |
| 2009/0186372 A1 * | 7/2009 | Bell | C12Q 1/006 435/26 |
| 2013/0075276 A1 * | 3/2013 | Hoashi | C12Q 1/004 205/777.5 |

FOREIGN PATENT DOCUMENTS

| | | |
|---|---|---|
| EP | 0238322 | 2/1992 |
| EP | 2211171 A1 | 7/2010 |
| JP | 2005-118014 A | 5/2005 |
| KR | 10-2002-0088521 A | 11/2002 |
| WO | 00/20626 A1 | 4/2000 |
| WO | WO2007056666 A2 | 5/2007 |
| WO | WO2009094297 A2 | 7/2009 |

OTHER PUBLICATIONS

Karyakin et al.,Electroanalysis, 1999, 11, 149-155.*
Lemmon et al., Anal. Chem, 1996, 68, 947-953.*
Vanysek, Peter, Electrochemcial Series.*
Kosela et al., Anal Bioanal Chem, 2002, 373:724-734.*
K. Tanaka et al., "Thionine and Ferric Chelate Compounds as Coupled Mediators in Microbial Fuel Cells", Bioelectrochemistry and Bioenergetics, 11 (1983) 289-297.
E. Katz et al., "Biochemical Fuel Cells", Handbook of Fuel Cells—Fundamentals, Technology and Applications, vol. 1: Fundamentals and Survey of Systems 2003 John Wiley & Sons.
A. Chaubey, et al., "Review Mediated Biosensors" Biosensors & Bioelectronics 17 (2002) 441-456.
T. Nakaminami, et al. "Electrochemical Oxidation of Cholesterol Catalyzed by Cholesterol Oxidase with Use of an Artificial Electron Mediator", Analytical Chemistry, vol. 69, No. 13, Jul. 1, 1997.

* cited by examiner

General name : Thionine
Chemical name : 7-imonophenothiazin-3-amine

Fig. 2

Thionine derivative (a) 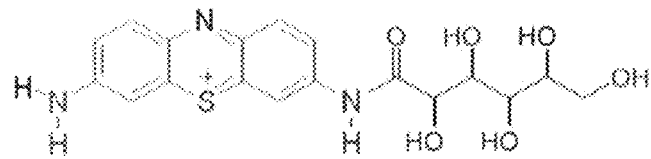

Chemical name:
3-amino-7-(2,3,4,5,6-pentahydroxyhexanamido)-5-phenothiazinium

Thionine derivative (b) 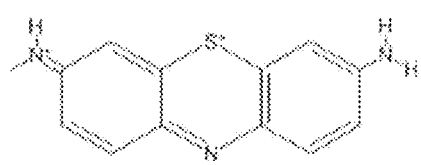

General name: Azure C
Chemical name: (7-amino-3-phenothiazinylidene)-methylammonium

Thionine derivative (c) 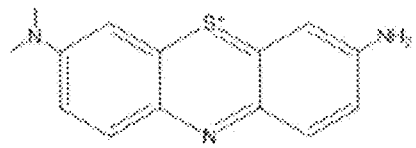

General name: Azure A
Chemical name: N',N'-dimethylphenothiazin-5-ium-3,7-diamine

Thionine derivative (d) 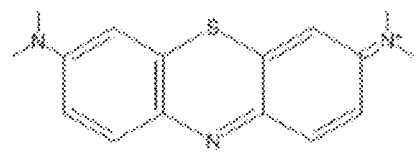

General name: Methylene Blue
Chemical name: 3,7-bis(dimethylamino)-phenothiazin-5-ium

Thionine derivative (e) 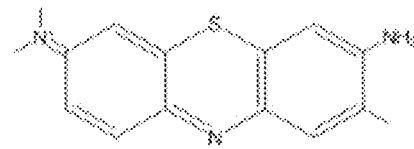

General name: Toluidine Blue
Chemical name:
(7-amino-8-methyl-phenothiazin-3-ylidene)-dimethyl-ammonium

COMPOSITION OF REDOX-REAGENTS FOR ELECTROCHEMICAL BIOSENSOR AND BIOSENSOR COMPRISING THE SAME

CROSS-REFERENCE TO RELATED APPLICATIONS

This patent application is a U.S. national phase under 35 U.S.C 371 of PCT/KR2012/007711 filed on Sep. 25, 2012, which claims the benefit of priority from Korean Patent Applications No. 10-2011-100018 and No. 10-2012-009668, filed on Sep. 30, 2011 and Jan. 31, 2012, respectively, the disclosure of which is incorporated herein by reference in its entirety.

BACKGROUND OF THE INVENTION

1. Field of the Invention

The present invention relates to a composition of redox-reagent for an electrochemical biosensor including metal-containing complex and thionine or derivative thereof as an electron transfer mediator, and a biosensor comprising the same.

2. Description of the Related Art

While a lot of efforts for improving the accuracy of a glucose meter for managing diabetes have been consistently made for the last thirty years, there are mainly two glucose measuring methods, i.e., spectrophotometer measurement and electrochemical measurement.

Between these two, the electrochemical measurement is more common, because its accuracy deterioration caused by blood-contamination onto a glucose meter is relatively less frequent and it requires smaller amount of blood.

Despite many researches associated with a glucose meter for such a long period of time, many problems still remain unsolved with regard to the accuracy of the glucose meter, and one of the problems is inherent to enzymes that are employed for the measurement.

For example, FAD-GOx, which is the most commonly used glucose redox enzyme for commercial electrochemical sensors, is stable under heat and has excellent specificity in enzymatic reaction, however, the measured glucose value is affected by the oxygen concentration in blood.

While a sensor based on PQQ-GDH enzyme is free from the oxygen influence, many monosaccharides and disaccharides including mannose, maltose, or lactose still affect the sensor (Igarashi, S., and Sode, K., Engineering PQQ glucose dehydrogenase with improved plate specificity-first site-directed mutagenesis studies on the active center of PQQ glucose dehydrogenase. Biomol. Engineer., 21, 81-89 (2004)), and more specifically, diabetes community has been keen on the effect of high maltose concentration found in diabetics (Mehmet, S., Quan, G., Thomas, S., and Goldsmith, D., Important causes of hypoglycemia in patients with diabetes on peritoneal dialysis. Diabet. Med., 18, 679-682 (2001)).

A NAD-GDH enzyme has excellent specificity on glucose reaction, however, its usage is inconvenient because it requires NAD+ or NADP+ be added to the reagent composition. As a solution to this inconvenience, an electrochemical sensor based on FAD-GDH (Enzyme Commission No. 1.1.99.10) has been developed.

The sensor based on FAD-GDH enzyme is not affected by the amount of oxygen in blood. Therefore, the sensor can be effectively applied to any blood sample collected from veins, arteries, or capillaries in human body. Although the sensor has a downside of reacting with xylose, it does not react with mannose, maltose or lactose, thus leaving it relatively superior to (PQQ-GDH)-based sensor with regard to glucose specific reaction.

The accuracy of a sensor is affected by not only the enzymes but also the electron transfer mediator. Potassium ferricyanide ($[K_3Fe(CN)_6]$), phenazine-methosulfate, methoxy phenazine-methosulfate, phenazine methyl sulfate and dichloroindophenol are well known for FAD-GDH's electron transfer mediator. However, the properties of all the above-mentioned mediators easily change at high temperature or humidity condition, leading to a tendency of accuracy deterioration in sensor when the sensor is stored for a long period of time. To address this problem, a method of replacing potassium ferricyanide with hydrophilic derivatives of phenothiazine was suggested (US 20090145775).

For an electrochemical sensor based on FAD-GOx (EC No. 1.1.3.4), hexaamineruthenium chloride ($[Ru(NH_3)_6Cl_3]$) has been employed as an electron transfer mediator because the sensor is much less affected from interfering substances such as uric acid and gentisic acid, and because its accuracy is much less deteriorated from moisture compared to a sensor employing ferricyanide (U.S. Pat. No. 7,288,174, US20090280551). However, because of fairly slow reaction between hexaamineruthenium chloride and FAD-GDH (EC No. 1.1.99.10), fabricating a useful sensor has not been easy Meanwhile, the following is a list of the examples—using two types of electron transfer mediators.

EP 0238322 A1 teaches a method of increasing the speed of electron transfer between bacteria and an electrode with ferricyanide and benzoquinone.

US 20070295616 A1 teaches a method of applying osmium (Os) and ferricyanide to a glucose sensor.

A. Amine et al. (A. Amine, J. M. Kauffmann, G. J. Patriarche, G. D. Christian; Characterization of mediated and non-mediated oxidase enzyme based glassy carbon electrode, Talanta, 1993, 40, 1157-1162.) teach a method of applying phenazine methosulfate and ferricyanide to glucose oxidase.

A. Amid and J. M Kauffman (A. Amine and J. M. Kauffmann; Preparation and characterization of a fragile enzyme immobilized carbon paste electrode, Bioelectrochem. Bioenerg., 1992, 28, 117-125.) teach a method of applying phenazine methosulfate and ferricyanide to glutamate dehydrogenase.

Yet, a secondary electron transfer mediator which can be used along with ruthenium complex has not been found.

In a research to find a solution to the problems mentioned above, the present inventors found that a reagent composition including metal-containing complex and thionine or derivatives thereof as an electron transfer mediator improves the efficiency of glucose detection by increasing the reaction speed between redox enzyme-thionine (or derivative thereof) and a metal-containing complex and that the reagent composition is hardly affected under high humidity condition and from interfering substances, and thus, completed the present invention.

PRIOR ARTS

Patent Documents

Patent Document 1: EP 00238322 A1
Patent Document 2: US 20070295616 A1

Non-Patent Documents

Non-patent Document 1: A. Amine, J. M. Kauffmann, G. J. Patriarche, G. D. Christian; Characterization of mediated and non-mediated oxidase enzyme based glassy carbon electrode, Talanta, 1993, 40, 1157-1162.

Non-patent Document 2: A. Amine and J. M. Kauffmann; Preparation and characterization of a fragile enzyme immobilized carbon paste electrode, Bioelectrochem. Bioenerg., 1992, 28, 117-125.

SUMMARY OF THE INVENTION

An objective of the present invention is to provide a composition of redox-reagent for an electrochemical biosensor including metal-containing complex and thionine or derivative thereof as an electron transfer mediator.

Another objective of the present invention is to provide a planar type biosensor in which a working electrode is coated with the redox-reagent.

Yet another objective of the present invention is to provide a converse type biosensor in which a working electrode is coated with the redox-reagent.

In order to achieve the objectives explained above, the present invention provides a composition of redox-reagent for an electrochemical biosensor including redox enzymes and an electron transfer mediator comprising metal-containing complex and thionine or derivative thereof.

Further, the present invention provides a planar type electrochemical biosensor in which a working electrode and a counter electrode are prepared coplanar, and the working electrode is coated with the redox-reagent.

Furthermore, the present invention provides a converse type electrochemical biosensor in which a working electrode and a counter electrode are prepared on two separate planes and the working electrode is coated with the redox-reagent.

According to the present invention, the redox-reagent including metal-containing complex and thionine or derivative thereof as an electron transfer mediator improves glucose sensitivity by increasing reaction speed among redox enzyme-thionine (or derivative thereof)—a metal-containing complex, and is hardly affected in high humidity condition and from interfering substances, and thus makes itself desirable for fabricating an electrochemical biosensor for blood glucose measurement.

BRIEF DESCRIPTION OF THE DRAWINGS

The foregoing and/or other aspects of the present invention will be more apparent upon reading the description of certain exemplary embodiments with reference to the accompanying drawings, in which:

FIG. 2 illustrates chemical structures of thionine derivatives used according to an embodiment of the present invention;

DETAILED DESCRIPTION OF THE INVENTION

Figure 1:
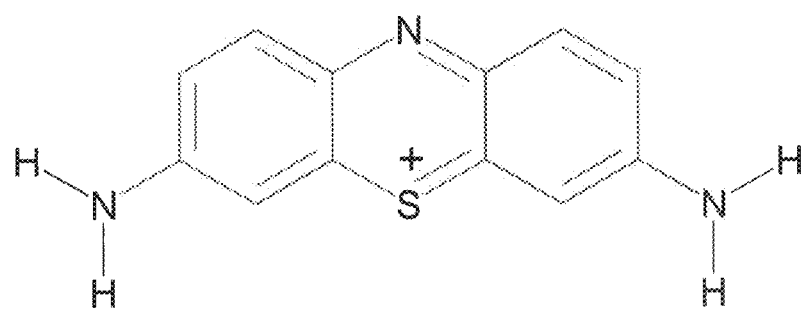
FIG. 1 illustrates a chemical structure of thionine used according to an embodiment of the present invention.

Hereinafter, the present invention will be explained in detail.

The present invention provides a composition of redox-reagent for an electrochemical biosensor including a redox enzyme and an electron transfer mediator, in which the electron transfer mediator includes a metal-containing complex and thionine or derivative thereof.

According to the composition of the redox-reagent of the present invention, the redox enzyme is reduced through reaction with its substrate, and the reduced enzyme and an electron transfer mediator react with each other to quantify the substrate.

Although the embodiments of the present invention are explained with reference to a biosensor for glucose measurement, similarly employing specific enzymes along with their appropriate mediators makes it possible to measure the concentration of various metabolites such as organic or inorganic substances such as cholesterol, lactate, creatinine, hydrogen peroxide, alcohol, amino acid or glutamate, or inorganic substance. Therefore, the present invention can be applied for quantifying various metabolites by switching the enzymes in the reagent composition.

For example, flavin adenine dinucleotide-glucose dehydrogenase (FAD-GDH), nicotinamide adenine dinucleotide-glucose dehydrogenase (NAD-GDH), glucose dehydrogenase (GDH), glutamate dehydrogenase, cholesterol oxidase, cholesterol esterase, lactate oxidase, ascorbic acid oxidase, alcohol oxidase, alcohol dehydrogenase or bilirubin oxidase may be used to perform the quantification of glucose, glutamate, cholesterol, lactate, ascorbic acid, alcohol, or bilirubin.

Meanwhile, the redox enzymes can be employed solely or along with their cofactors. The cofactors play a role of storing hydrogen which the redox enzymes obtained from their substrates. The cofactors may be FAD (flavin adenine dinucleotide) or NAD (nicotinamide adenine dinucleotide).

In the formulation of the redox-reagent of the present invention, the electron transfer mediator is reduced from a redox-reaction with the reduced enzyme which is produced from the reaction with its substrate. The formed electron transfer mediator in reduction state generates current at the surface of the electrode onto which oxidation potential is applied.

Herein, the metal-containing complex and thionine or derivative thereof are mixed to be used as the electron transfer mediator, but this does not mean to exclude the usage of traditional substances such as ferrocene, ferrocene derivatives, quinone, quinone derivatives, organic conducting salt, and viologen.

For the above electron transfer mediator, ruthenium complex or ferricyanide complex may be used as metal-containing complex. The ruthenium complex may include $Ru(NH_3)_6C_{13}$, $[Ru(2,2',2''\text{-terpyridine})(1,10\text{-phenanthroline})(OH_2)]^{2+}$, trans-$[Ru(2,2'\text{-bipyridine})_2(OH_2)(OH)]^{2+}$, $[(2,2'\text{-bipyridine})_2(OH)RuORu(OH)(2,2'bpy)_2]^{4+}$ or $[Ru(4,4'\text{-bipyridine})(NH_3)_5]^{2+}$, and ferricyanide complex may include $K_3Fe(CN)_6$.

For the above electron-transfer mediator, the thionine derivatives may include 3-amino-7-(2,3,4,5,6-pentahydroxyhexanamido)-5-phenothiazinium (thionine derivative a), azure C (thionine derivative b), azure A (thionine derivative c), methylene blue (thionine derivative d), toluidine blue (thionine derivative e) (See FIG. 2).

Hexaamineruthenium chloride is the most preferred ruthenium complex in the present invention, because its redox state is stable and reversible in an aqueous solution; the reduced electron transfer mediator thereof does not react with oxygen; the oxidation of the reduced electron transfer mediator is not sensitive to pH; and interfering substances such as acetaminophene, ascorbic acid, bilirubin, dopamine, uric acid and gentisic acid do not react with hexaamineruthenium chloride (See Experimental Example 4).

According to the present invention, the electrode transfer mediator of ruthenium complexes along with thionine significantly improves glucose detection efficiency and high humidity and various interferants hardly affect glucose detection thereof.

For example, referring to Comparative Example 1, when hexaamineruthenium chloride ($Ru(NH_3)_6Cl_3$) is solely used as an electron transfer mediator without thionine, the mediator is hardly applicable to a biosensor because its reaction rate with the redox enzyme is slow. On the contrary, when the metal-containing complex and thionine or its derivative are used together as electron transfer mediator according to the present invention, because of the fast reaction rate between redox enzyme and thionine or its derivative and between thionine or its derivative and metal-containing complex, the mediator can be effectively used for a biosensor fabrication (Experimental Example 1).

The composition of the redox-reagent according to the present invention preferably contains 250 to 340 wt. % of metal-containing complex per 100 wt. % of redox enzyme. When the reagent contains less than 250 wt. % of metal-containing complex, the sensor sensitivity degrades at high glucose concentration, while when the reagent contains more than 340 wt. % of metal-containing complex, the reagent does not dissolve quickly in blood.

The composition of the redox-reagent according to the present invention preferably contains 6 to 20 wt. % of thionine or derivative thereof per 100 wt. % of redox enzyme. When the reagent contains less than 6 wt. % of thionine or a derivative thereof, the sensor sensitivity degrades at high glucose concentration, while when the reagent contains more than 20 wt. % of thionine or a derivative thereof, the reagent does not dissolve quickly in blood.

Meanwhile, the composition of the redox-reagent according to the present invention may additionally include additives such as surfactant, water-soluble polymer, quaternary ammonium salt, fatty acid and thickener.

The surfactant used as an additive causes the reagent to evenly spread on the electrode to a uniform thickness during reagent dispensing. The surfactant may include Triton X-100, sodium dodecyl sulfate, perfluorooctane sulfonate, or sodium stearate. According to the present invention, the composition of the redox-reagent preferably contains 10 to 25 wt. % of the surfactant per 100 wt. % of redox enzyme.

The water-soluble polymer used as an additive plays a role as a polymer scaffold, which assists stabilization and dispersion of the enzyme. The water-soluble polymer may include, for example, polyvinyl pyrrolidone (PVP), polyvinyl alcohol (PVA), perfluoro sulfonate, hydroxyethyl cellulose (HEC), hydroxypropyl cellulose (HPC), carboxy methyl cellulose (CMC), cellulose acetate, or polyamide. The composition of the redox-reagent according to the present invention preferably contains 30 to 70 wt. % of the water-soluble polymer per 100 wt. % of redox enzyme.

The quaternary ammonium salt used as an additive reduces measurement error from hematocrit. The quaternary ammonium salt may include, for example, ecyltrimethylammonium, myristyltrimethylammonium, cetyltrimethylammonium, octadecyltrimethylammonium, or tetrahexylammonium. The composition of the redox-reagent according to the present invention preferably contains 70 to 130 wt. % of quaternary ammonium salts per 100 wt. % of redox enzyme.

The fatty acid used as an additive also reduces hematocrit-related measurement error as the quaternary ammonium salt does, and also extends the linear dynamic range of the biosensor at high concentration. The fatty acid may include $C_4$~$C_{20}$ fatty acid or salt thereof, or preferably, fatty acid of $C_6$~$C_{12}$ alkyl chain or salt thereof. The fatty acid may include, for example, caproic acid, heptonic acid, caprylic acid, octanoic acid, nonanoic acid, capric acid, undecanoic acid, lauric acid, tridecanoic acid, myristic acid, pentadecanoic acid, palmitic acid, heptadecanoic acid, stearic acid, nonadecanoic acid, or arachidonic acid. The composition of the redox-reagent according to the present invention preferably contains 30 to 70 wt. % of the fatty acid per 100 wt. % of redox enzyme.

The thickener used as an additive securely attaches the reagent onto the electrode. The thickener may include, for example, Natrosol, or DEAE-dextran hydrochloride. The composition of the redox-reagent according to the present invention preferably contains 30 to 90 wt. % of the thickener per 100 wt. % of redox enzyme.

According to the present invention, the electrochemical biosensor may be a planar type biosensor in which a working electrode and a counter electrode are prepared in one plane, and the composition of redox-reagent according to the present invention is coated on the working electrode.

Furthermore, according to the present invention, the electrochemical biosensor may be a converse type biosensor in which a working electrode and a counter electrode are prepared in separate planes and faced with each other, and the composition of the redox-reagent according to the present invention is coated on the working electrode.

The planar and converse type electrochemical biosensors may be fabricated by the known methods disclosed in Korean Patent Applications Nos. 10-2003-0036804, 10-2005-0010720, 10-2007-0020447, 10-2007-0021086, 10-2007-0025106, and 10-2007-0030346, and E. K. Bauman et al. (Analytical Chemistry, vol 37, p 1378, 1965), and K. B. Oldham in ("Microelectrodes: Theory and Applications," Kluwer Academic Publishers, 1991).

Hereinafter, the planar and the converse type biosensors will be explained in detail by referring to FIGS. 3 and 4.

Figure 3:
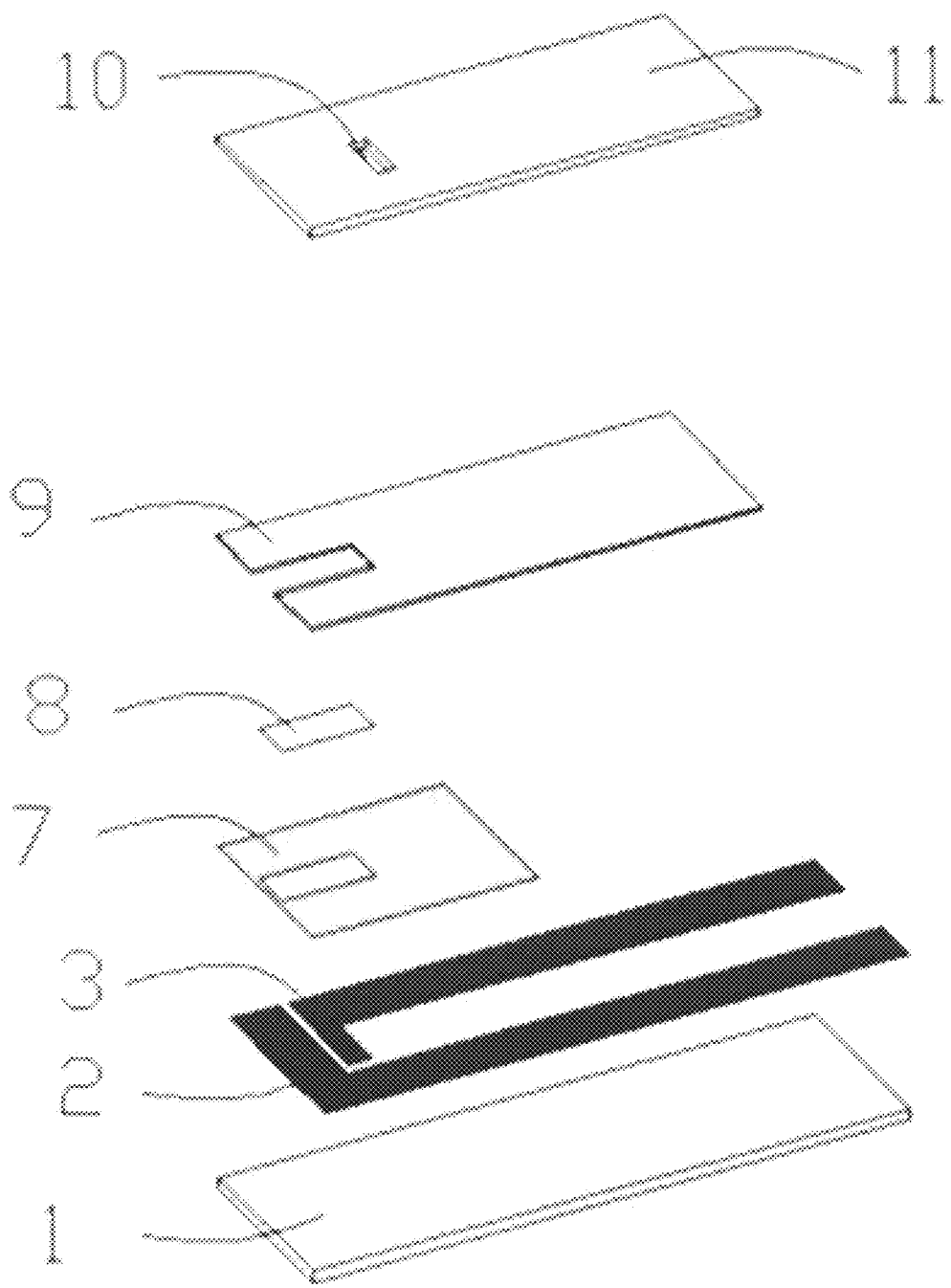
FIG. 3 is an exploded view illustrating a planar type biosensor according to Examples of the present invention.

Referring to FIG. 3, the planar type electrochemical biosensor, in which the working electrode 2 and the counter electrode 3 are prepared in one plane, has a sequentially-stacked structure of: a top layer 11 having a channel 10 through which blood is drawn into the sensor; a spacer 9 coated with adhesive on both surfaces thereof to attach the top layer 11 and the bottom layer thereto causing the blood to be drawn toward the electrode by capillary action; a composition of the redox-reagent 8 according to the present invention coated on the working electrode 2 to be explained below; an insulating layer 7 having a passage to define areas of the working electrode 2 and the counter electrode 3; the working electrode 2 and the counter electrode 3 printed on the bottom layer 1; and the bottom layer 1 on which the working electrode 2 and the counter electrode 3 are formed.

Figure 4:
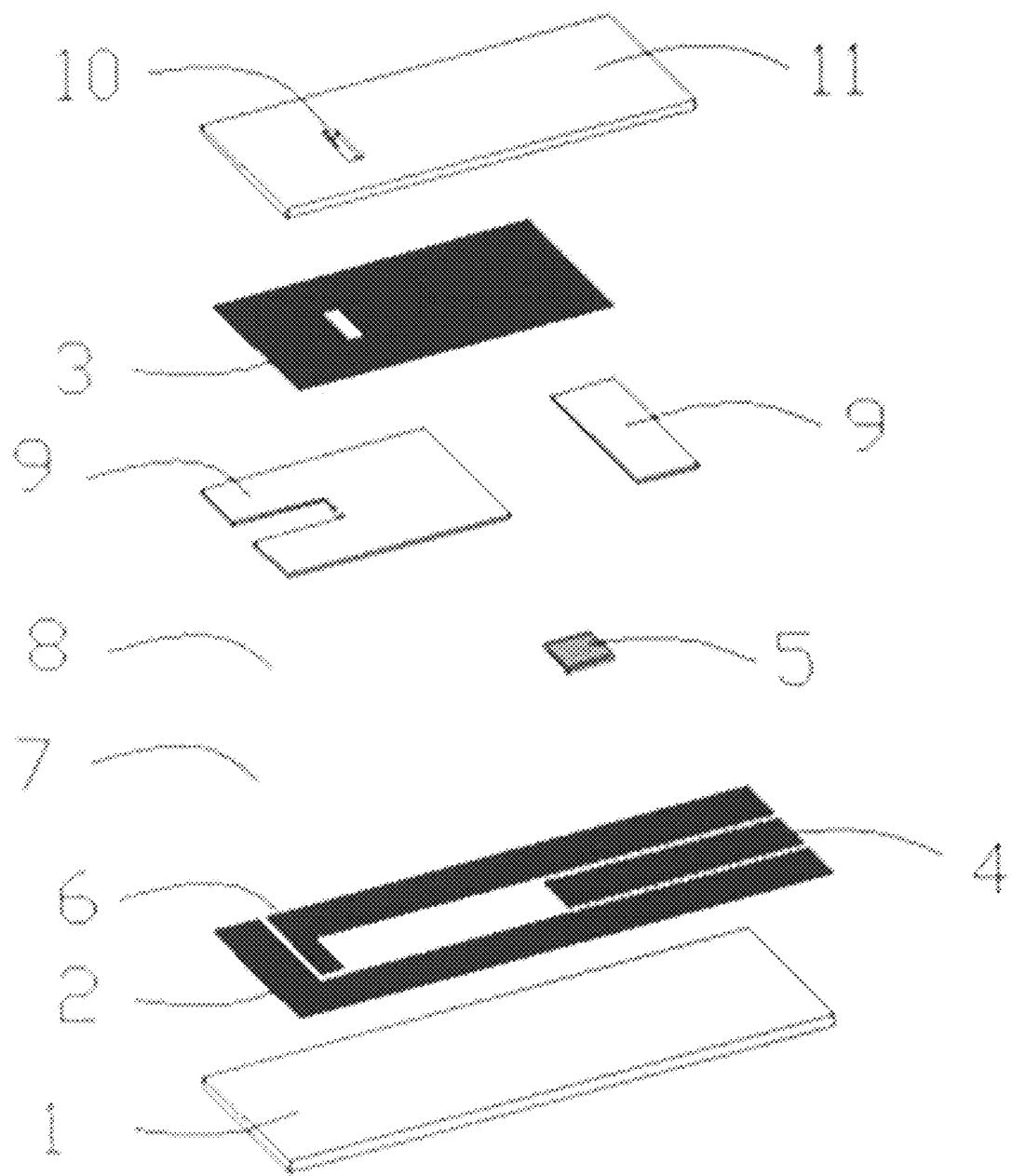
FIG. 4 is an exploded view illustrating a converse type biosensor according to an embodiment of the present invention.

Referring to FIG. 4, the converse type electrochemical biosensor, in which the working electrode 2 and the counter electrodes 3 are prepared in separate planes to face each other, has the sequentially-stacked structure of: the top layer 11 which has a channel 10 through which blood is drawn into the sensor and on which the counter electrode 3 is printed; the counter electrode 3 printed on the top layer 11; the spacer 9 coated with adhesive on both surfaces thereof to attach the top layer 11 and the bottom layer 1 thereto to cause blood to be drawn toward the electrode by capillary action; a composition of the redox-reagent 8 according to the present invention coated on the working electrode 2; an insulating layer 7 having a passage to define the area of the working electrode 2 and the counter electrode 3; a circuit connect ground 5 to connect the counter electrode 3 to the lead 4 of the counter electrode 3; the working electrode 2, the lead 4 of the counter electrode 3 and a flow rate detecting electrode 6 to measure the velocity of introduced blood, all of which being printed on the bottom layer; and the bottom layer 1 on which the working electrode 2, the lead 4 of the counter electrode 3 and the flow rate detecting electrode 6 are formed.

As explained above, the composition of redox-reagent containing metal-containing complex and thionine or its derivative as electron transfer mediators according to the present invention can be usefully implemented in the manufacture of electrochemical biosensors for measurement of glucose level in blood, because the composition of redox-reagent according to the present invention increases reaction rate between redox enzyme—thionine (or its derivative)—metal-containing complex and greatly increased glucose detection rate, and also is hardly affected from high humidity or interfering substances.

EXAMPLES

Hereafter, the present invention will be explained in detail with reference to examples and experimental examples. However, the examples are written only for illustrative purpose, and accordingly, the present invention is not limited to any specific examples.

<Example 1> Preparation of a Composition of Redox-Reagent Including Hexaamineruthenium Chloride and Thionine as an Electron-Transfer Mediator Per 100 wt. % of flavin adenine dinucleotide-glucose dehydrogenase (FAD-GDH) as the redox enzyme, 290.4 wt. % of hexaamineruthenium chloride ($Ru(NH_3)_6Cl_3$) as the metal-containing complex; 14.6 wt. % (8 mM) or 18.3 wt. % (10 mM) of thionine; 52 wt. % of sodium octanoate as the fatty acid; 104.3 wt. % of myristyltrimethylammonium bromide as the quaternary ammonium salt; 11.7 wt. % of DEAE-dextran hydrochloride and 52 wt. % of Natrosol as the thickener; 52 wt. % of polyvinyl alcohol as the water-soluble polymer; and 17.4 wt. % of the surfactant (Triton X-100); were dissolved in the sodium phosphate buffer solution (pH 6.4, 1249 ml of 0.1 M) and deionized water (1614.6 ml), and solid particles remaining in the solution were filtered out. The solution was placed in the syringe of a pneumatic dispenser (EFD XL100) until use thereof.

Two reagent compositions were prepared, one containing 8 mM and the other containing 10 mM of thionine content, respectively. Hereinbelow, thionine content is indicated in parenthesis whenever the composition of reagents of Example 1 is recited.

<Example 1-1> Fabrication of a Converse Type Biosensor Containing the Reagent Composition of Example 1

Referring to FIG. 4, a converse type biosensor having an average of 0.5 μl sample introducing portion was prepared. The converse type biosensor was prepared by referring to the methods disclosed in Korean Patent Applications Nos. 10-2003-0036804, 10-2005-0010720, 10-2007-0020447, 10-2007-0021086, 10-2007-0025106, and 10-2007-0030346, and E. K. Bauman et al. in Analytical Chemistry, vol 37, p 1378, 1965, and K. B. Oldham in "Microelectrodes: Theory and Applications," Kluwer Academic Publishers, 1991.

Referring to FIG. 4, reference numeral 1 denotes a bottom layer plastic formed from polyester on which a working electrode (area: 1.95 mm2), a lead of a counter electrode, and a flow rate detecting electrode are screen-printed; 2, 3, 4, 6 denote electrodes formed by screen-printing carbon graphite, in which reference numeral 2 denotes working electrode, 3 is counter electrode, 4 is the lead of the counter electrode, and 6 is a viscosity measuring electrode for measuring the velocity of incoming blood; 5 is a circuit connecting ground formed from silver and silver chloride (Ag/AgCl) for connecting the working and counter electrodes 3 and 4; 7 is an insulator which defines the area of the working electrode 2; 8 is the composition of redox reagent (thionine 8 mM or 10 mM) prepared at Example 1 and coated on the working electrode 2; 9 is a spacer with 0.07 mm thickness through which blood is drawn toward the electrode by capillary action, and on which adhesive is coated on both surfaces to bond the top and bottom layers; 10 is an air vent; and 11 is a top layer plastic formed from polyester on which the counter electrode is screen-printed.

Hereinbelow, in explaining the converse type biosensor of Example 1-1, the thionine content of the reagent composition of Example 1 will be also identified in parenthesis.

<Example 1-2> Fabrication of a Planar Type Biosensor Containing the Reagent Composition of Example 1

Referring to FIG. 3, a planar type biosensor having an average of 0.5 μl sample introducing portion was prepared. The planar type biosensor was particularly fabricated according to the methods disclosed in the Korean Patent Applications Nos. 10-2003-0036804, 10-2005-0010720, 10-2007-0020447, 10-2007-0021086, 10-2007-0025106, and 10-2007-0030346, and E. K. Bauman et al. in Analytical Chemistry, vol 37, p 1378, 1965, and K. B. Oldham in "Microelectrodes: Theory and Applications," Kluwer Academic Publishers, 1991.

Referring to FIG. 3, reference numeral 1 denotes a bottom layer plastic formed from polyester including a working electrode (area: 1.05 $mm^2$) and a counter electrode formed thereon; 2 and 3 are electrodes made by screen printing carbon graphite, in which 2 is a working electrode and 3 is a counter electrode; 7 is an insulator which defines the area of the working electrode and the counter electrode; 8 is the composition of redox-reagent (thionine 8 mM or 10 mM) prepared at Example 1 and coated on the working electrode; 9 is a spacer of 0.10 mm thickness through which blood is drawn toward the electrode by capillary action, and on which adhesive is coated on both surfaces to bond the top and bottom layers; 10 is an air vent for drawing blood into the sensor; and 11 is a top layer plastic formed from polyester.

Hereinbelow, in explaining the planar type biosensor of Example 1-2, the thionine content of the reagent composition of Example 1 will be also identified in parenthesis.

<Example 2> Preparation of Composition #1 of Redox-Reagent Containing Hexaamineruthenium Chloride and a Derivative of Thionine as an Electron Transfer Mediator The reagent composition was prepared in the same manner as the one explained above in Example 1, except for the fact that the thionine of reagent composition of Example 1 was replaced by 3-amino-7-(2,3,4,5,6-pentahydroxyhexanamido)-5-phenothiazinium ('thionine derivative a'), which is one of the derivatives of thionine listed in FIG. 2.

<Example 2-1> Fabrication of a Converse Type Biosensor Containing the Reagent Composition of Example 2

The converse type biosensor was fabricated in the same manner as the one explained above, except for using the reagent composition of Example 2 instead of Example 1 coated on the working electrode of Example 1-2.

<Example 3> Preparation of Composition #2 of Redox-Reagent Containing Hexaamineruthenium Chloride and a Derivative of Thionine as an Electron Transfer Mediator The reagent composition was prepared in the same manner as the one explained in Example 1, except for using 10 mM azure C ('thionine derivative b'), which is one of the thionine derivatives listed in FIG. 2, instead of the thionine.

<Example 3-1> Fabrication of a Converse Type Biosensor Containing the Reagent Composition of Example 3

A converse type biosensor was fabricated in the same manner as the one explained in Example 1-1, except for using the reagent composition of Example 3 instead of Example 1 on the working electrode.

<Example 4> Preparation of Composition #3 of Redox-Reagent Containing Hexaamineruthenium Chloride and a Derivative of Thionine as an Electron Transfer Mediator The reagent composition was prepared in the same manner as the one explained in Example 1, except for using 10 mM azure A ('thionine derivative c'), one of the thionine derivatives listed in FIG. 2, instead of thionine.

<Example 4-1> Fabrication of a Converse Type Biosensor Containing the Reagent Composition of Example 4

A converse type biosensor was fabricated in the same manner as the one explained in Example 1-1, except for using the reagent composition of Example 4 instead of Example 1.

<Example 5> Preparation of Composition #4 of Redox-Reagent Containing Hexaamineruthenium Chloride and a Derivative of Thionine The reagent composition was prepared in the same manner as the one explained in Example 1, except for using 10 mM methylene blue ('thionine derivative d'), one of the thionine derivatives listed in FIG. 2, instead of the thionine.

<Example 5-1> Fabrication of a Converse Type Biosensor Containing the Reagent Composition of Example 5

A converse type biosensor was fabricated in the same manner as explained in Example 1-1, except for using the reagent composition of Example 5 instead of Example 1 on the working electrode.

<Example 6> Preparation of Composition #5 of Redox-Reagent Containing Hexaamineruthenium Chloride and Derivative of Thionine as an Electron Transfer Mediator The reagent composition was prepared in the same manner as the one explained in Example 1, except for using 10 mM Toluidine Blue ('thionine derivative e'), one of the thionine derivatives listed in FIG. 2, instead of the thionine.

<Example 6-1> Fabrication of a Converse Type Biosensor Containing the Reagent Composition of Example 6

A converse type biosensor was fabricated in the same manner as explained in Example 1-1, except for using the reagent composition of Example 6 instead of Example 1 on the working electrode.

<Example 7> Preparation of Composition of Redox-Reagent Containing Potassium Ferricyanide and Thionine as an Electron Transfer Mediator Reagent composition was prepared in the same manner as the one explained in Example 1, except for using potassium ferricyanide ($K_3Fe(CN)_6$) and thionine instead of hexaamineruthenium chloride ($Ru(NH_3)_6Cl_3$).

<Example 7-1> Fabrication of a Converse Type Biosensor Containing the Reagent Composition of Example 7

A converse type biosensor was fabricated in the same manner as explained in Example 1-1, except for using the reagent composition of Example 7 instead of Example 1 on the working electrode.

<Comparative Example 1> Preparation of Composition of Redox-Reagent Containing Hexamineruthenium Chloride as an Electron Transfer Mediator Reagent composition was prepared in the same manner as the one explained in Example 1, except for not using thionine.

<Comparative Example 1-1> Fabrication of a Converse Type Biosensor Containing the Reagent Composition of Comparative Example 1

A converse type biosensor was fabricated in the same manner as explained in Example 1-1, except for using the reagent composition of Comparative Example 1 instead of Example 1 on the working electrode.

<Comparative Example 2> Preparation of Composition of Redox-Reagent Containing Potassium Ferricyanide as an Electron Transfer Mediator Reagent composition was prepared in the same manner as the one explained in Example 1, except for using potassium ferricyanide ($K_3Fe(CN)_6$) instead of hexaamineruthenium chloride ($Ru(NH_3)_6Cl_3$) and thionine.

<Comparative Example 2-1> Fabrication of a Converse Type Biosensor Containing the Reagent Composition of Comparative Example 2

A converse type biosensor was fabricated in the same manner as explained in Example 1-1, except for using the reagent composition prepared at Comparative Example 2 instead of Example 1 on the working electrode.

<Experimental Example 1> Current Measurement Using a Converse Type Biosensor with Glucose Standard Solution Current for glucose standard solution was measured, using the converse type biosensor fabricated at Example 1-1 (10 mM of thionine) and the converse type biosensor fabricated at Comparative Example 1-1. Here, the 'glucose standard solution' refers to the blood sample derived from intravenous blood that is adjusted to 42% hematocrit and several glucose concentration using glucose analyzer (Manufacturer: YSI, Model name: 2300 Stat Plus).

Figure 5:
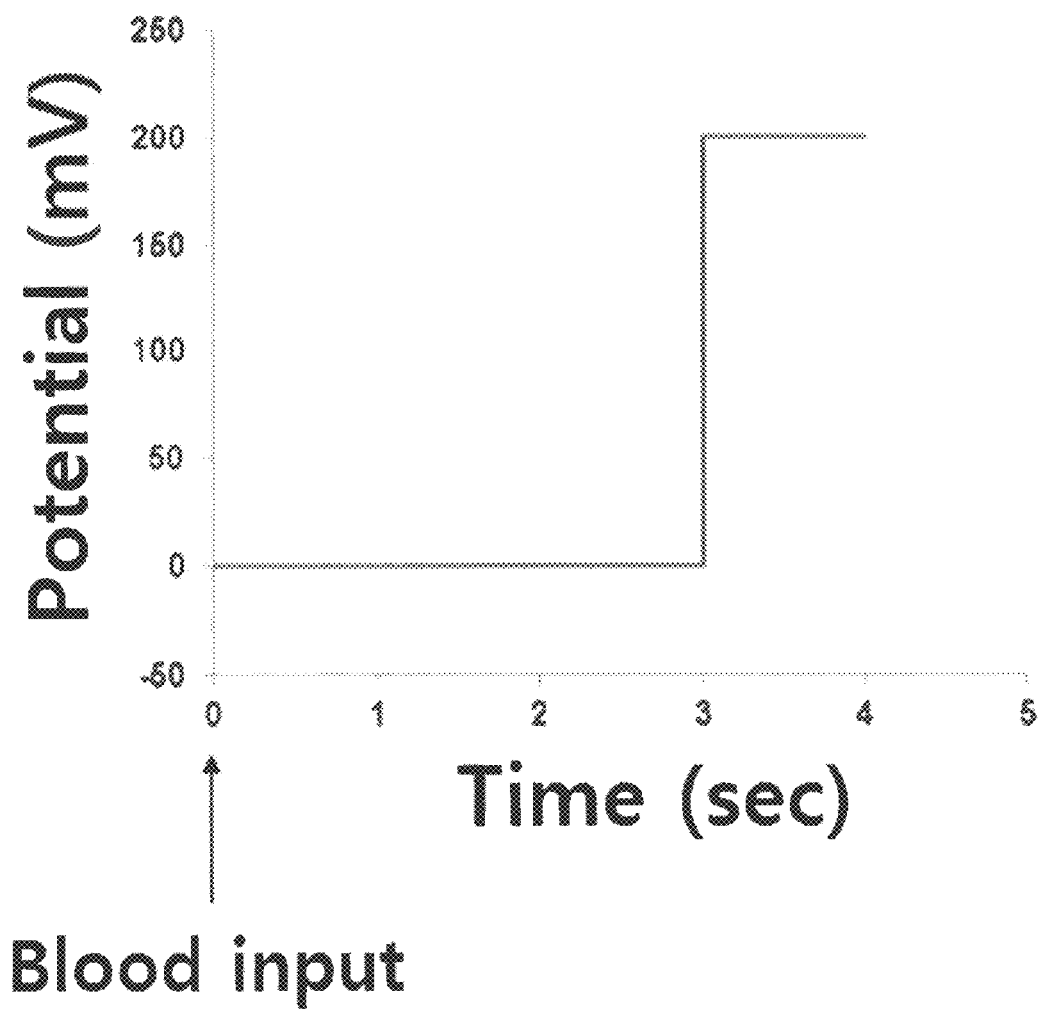
FIG. 5 is a graph illustrating voltage variations relative to time applied to the working electrode of the biosensor according to one embodiment of the present invention. When a sample concurrently covers both the working electrode and the counter electrode, the working electrode is set to 0 mV. After three seconds, 200 mV is applied to the working electrode, and current is measured at 4 seconds.

To be specific, the working electrode was applied at 0 mV at a moment when each standard solution of 69, 97, 148, 201, 304, 399 or 503 mg/dL glucose concentration covered both the working electrode and the counter electrode, and after three second wait, the working electrode was applied at 200 mV, and current was measured after one second (see FIG. 5). The measurement was performed ten times per glucose concentration and the average values are listed in FIG. 6.

The sample amount of 0.5 µl was applied to the introducing portion of the converse type biosensor of Example 1-1 and Comparative Example 1-1, and it took about 0.2 second or less until the whole blood of 42% hematocrit filled the introducing portion.

FIG. 5 is a graph illustrating voltage variations relative to time applied to working electrode of the biosensor according to one embodiment of the present invention: When a sample concurrently covers both the working electrode and the counter electrode, working electrode is applied at 0 mV. After three seconds, 200 mV is applied to the working electrode, and current is measured at 4 seconds.

Figure 6:
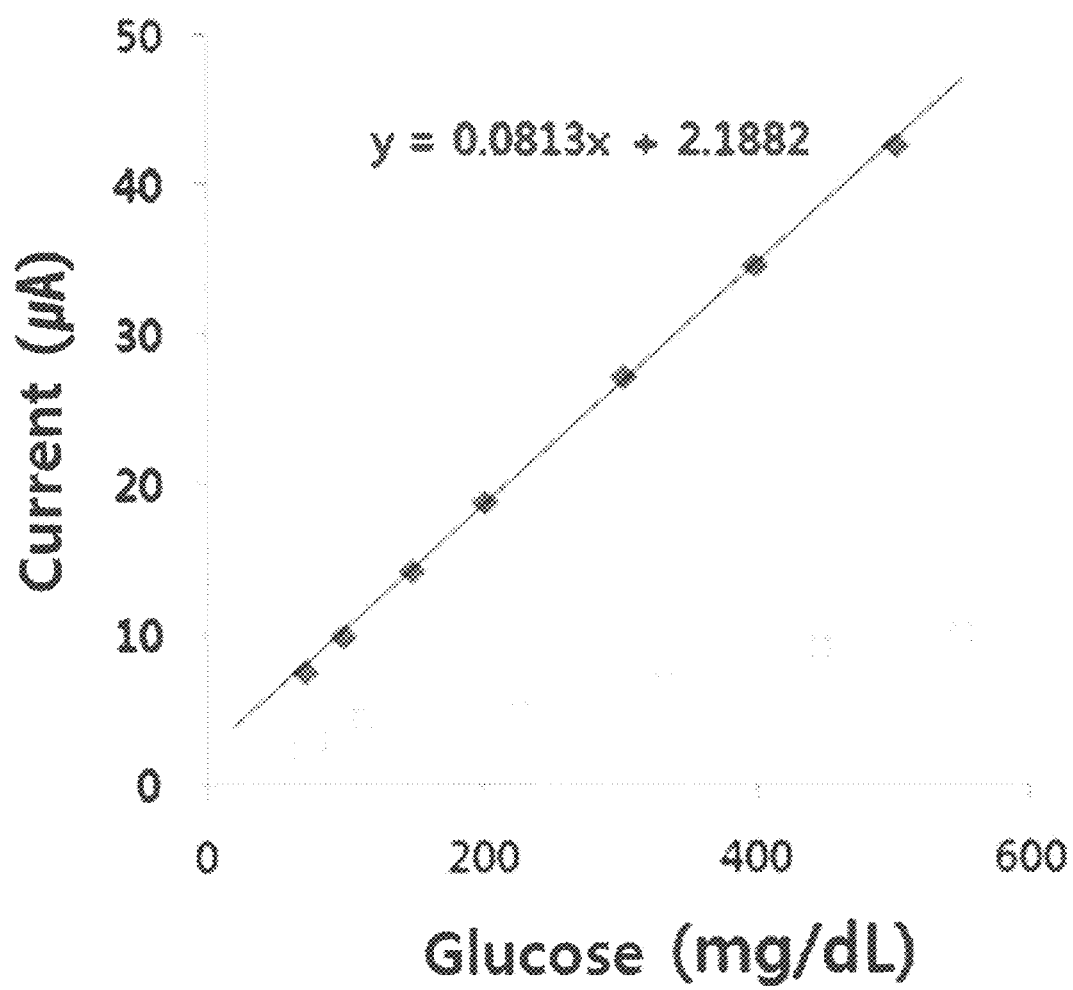
FIG. 6 is a graph showing current measured with the samples of several glucose concentration using the converse type biosensors according to Example 1-1 and Comparative Example 1-1.

FIG. 6 is a graph illustrating the current measured as a function of glucose concentration using the converse type biosensors of Example 1-1 and Comparative Example 1-1.

Referring to FIG. 6, the converse type biosensor of Example 1-1, which contains both hexaamineruthenium chloride and thionine as an electron transfer mediator, exhibited good linearity in which the measured current gradually increases with glucose concentration. But the converse type biosensor of Comparative Example 1-1, containing hexamineruthenium chloride only (i.e., without thionine) as an electron transfer mediator showed poor linearity for glucose concentrations. The slope of the electric current per unit area of the working electrode measured using the converse type biosensor of Example 1-1 was 41.7 nA/mm$^2$/(mg/dL), meaning very high reaction rate with glucose.

Accordingly, because the converse type biosensor applied with the redox reagent according to the present invention reacts very rapidly with glucose, the composition of the redox-reagent according to the present invention is very useful in fabricating a biosensor for detecting glucose in blood.

<Experimental Example 2> Current Measurement Using Planar Type Biosensor with Glucose Standard Solution Current was measured with glucose standard solution in the same manner as explained in Experimental Example 1, using the planar type biosensor (8 mM of thionine) of Example 1-2.

Figure 7:
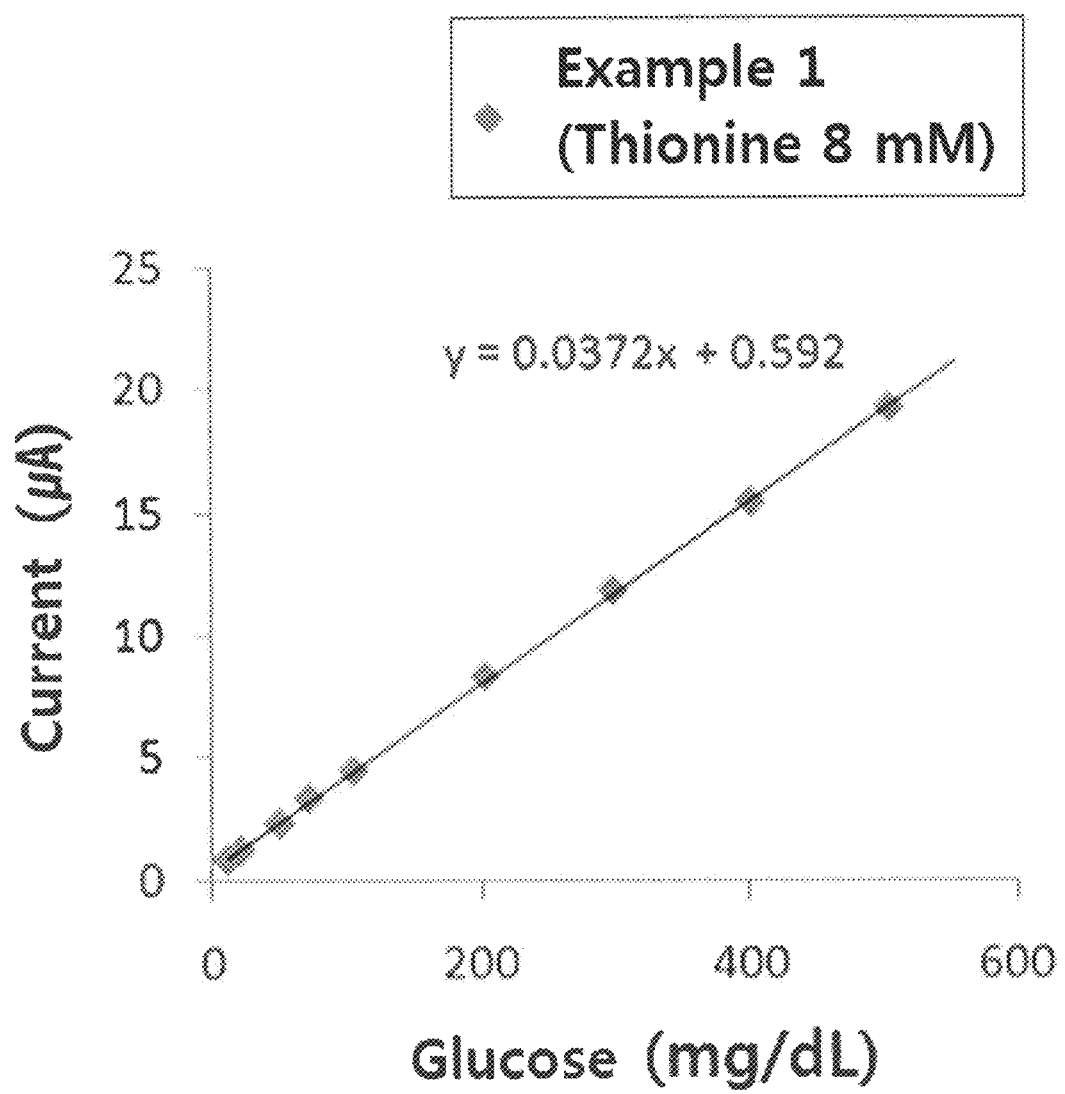
FIG. 7 is a graph showing current measured with the samples of several glucose concentration using the planar type biosensors according to Example 1-2.

FIG. 7 is a graph showing the current measured as a function of glucose concentration using the planar type biosensors according to Example 1-2.

Referring to FIG. 7, similarly to the converse type biosensor of Example 1-1 used in the Experimental Example 1, the planar type biosensor of Example 1-2 also exhibited good linearity in that the measured current gradually increases with glucose concentration. The slope of the current measured using the planar type biosensor according to Example 1-2 was 35.4 nA/mm$^2$/(mg/dL) per unit area of the working electrode, thus exhibiting very high reaction rate with glucose.

Accordingly, because the composition of the redox-reagent according to the present invention applied to the planar type biosensor reacts very rapidly with glucose, the composition is very useful in fabricating a biosensor for detecting glucose in blood.

<Experimental Example 3> Current Measurement Using the Converse Type Biosensor According to Examples 2-1 to 6-1 with Glucose Standard Solution Current was measured with the glucose standard solution in the same manner as explained in Experimental Example 1, using the converse type biosensor of Examples 2-1 to 6-1 coated with thionine derivatives of FIG. 2, and using the converse type biosensor (10 mM of thionine) of Example 1-1.

To be specific, thionine dissolves up to 10 mM at maximum without generating sediment in the reagent composition in the condition of Example 1. On the contrary, 3-amino-7-(2,3,4,5,6-pentahydroxyhexanamido)-5-phenothiazinium ('thionine derivative a') having five hydrophilic (—OH) groups used in Example 2 can dissolve up to approximately 50 mM without generating sediment. Consequently, the converse type biosensor of Example 1-1 and Examples 3-1 to 6-1 contained 10 mM thionine or its derivatives ('thionine derivatives b to e'), and the converse type biosensor of Example 2-1 used 50 mM of thionine derivative a.

Figure 8:
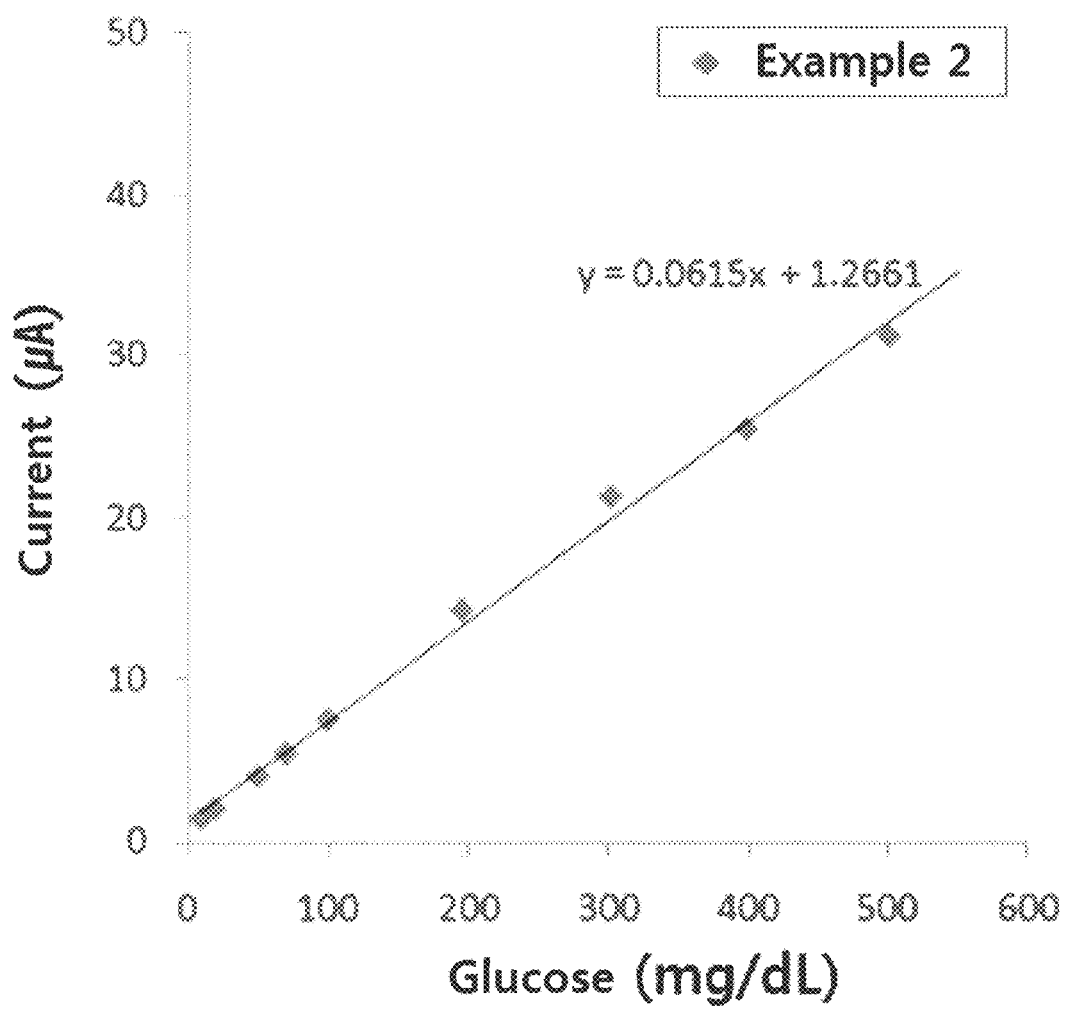
FIG. 8 is a graph showing current measured with the samples of several glucose concentration using the converse type biosensors according to Example 2-1.

FIG. 8 is a graph showing the current measured with the samples of several glucose concentration using the converse type biosensor of Example 2-1.

Figure 9:
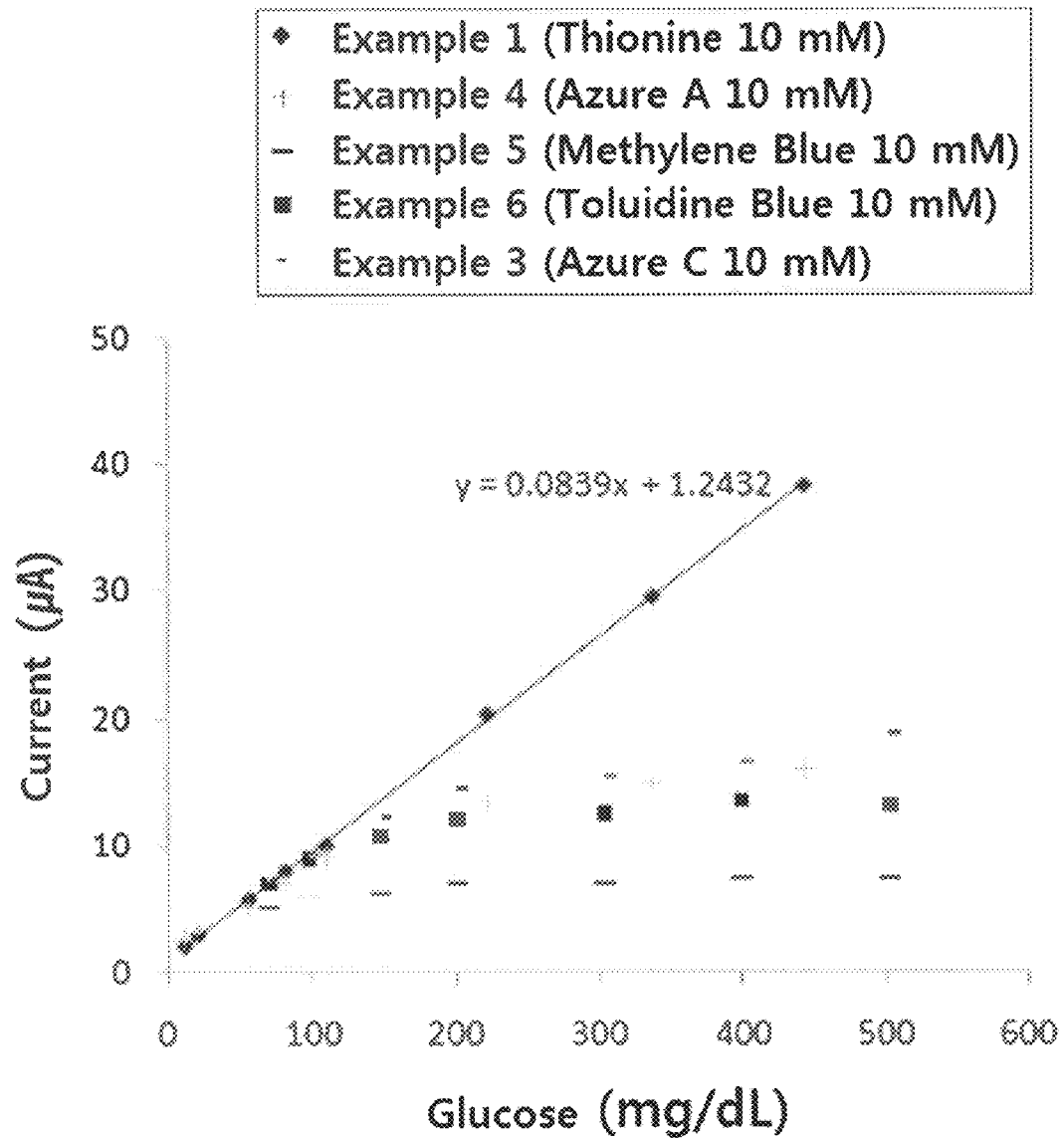
FIG. 9 is a graph showing current measured with the samples of several glucose concentration using the converse biosensors according to Example 1-1 (10 mM-thionine) and Examples 3-1 to 6-1.

FIG. 9 is a graph showing the current measured with the samples of several glucose concentration using the converse biosensors according to Example 1-1 (10 mM-thionine) and Examples 3-1 to 6-1.

Referring to FIGS. 8 and 9, the converse type biosensor containing thionine derivative a according to Example 2-1 showed current slope of 31.5 nA/mm$^2$/(mg/dL) per unit area of working electrode, thus indicating high reaction rate with glucose. The current by the converse type biosensor of Example 2-1 showed noticeably higher slope than those of the converse type biosensors containing thionine derivatives b to e according to Examples 3-1 to 6-1.

Accordingly, because the composition of the redox-reagent according to the present invention applied to the converse type biosensor reacts very rapidly with glucose, the composition is very useful in fabricating a biosensor for detecting glucose in blood.

<Experimental Example 4> Evaluation on the Influence from Interfering Substance Depending on the Choice of Electron Transfer Mediator In order to investigate the degree of interference from the severely interfering substances such as acetaminophene, ascorbic acid, bilirubin, dopamine, uric acid and gentisic acid among the substances listed by the Clinical Laboratory Standards Institute (CLSI), the following test was conducted using the converse type biosensor (8 mM of thionine) of Example 1-1 and converse type biosensor of Comparative Example 2-1.

To be specific, current was measured with 80 mg/dL glucose sample. Next, current was measured with the samples that are respectfully spiked with acetaminophene (20 mg/dL), ascorbic acid (20 mg/dL), bilirubin (40 mg/dL), dopamine (2.5 mg/dL), uric acid (20 mg/dL) and gentisic acid (50 mg/dL). The difference in current between before and after spiking the interferants was then converted into glucose value and its outcome is tabulated as below.

TABLE 1

| Interfering substance | Concentration (mg/dL) | Difference in the measured values (mg/dL) | |
|---|---|---|---|
| | | Ex. 1-1 | Comp. Ex. 2-1 |
| acetaminophene | 20 | −0.1 | 26.2 |
| ascorbic acid | 20 | 9.8 | 38.2 |
| bilirubin | 40 | −1.6 | 30.9 |
| Dopamine | 2.5 | 2.2 | 53.8 |
| uric acid | 20 | −0.8 | 27.2 |
| gentisic acid | 50 | 5.6 | 98.5 |

As shown in Table 1, in case of Example 1-1, the influence from all interferants was significantly lower compared to Comparative Example 2-1.

Accordingly, because the composition of the redox-reagent according to the present invention is hardly influenced by the interfering substances, the composition is very useful in fabricating a biosensor for detecting glucose in blood.

The foregoing embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims, and many alternatives, modifications, and variations will be apparent to those skilled in the art.

What is claimed is:

1. A composition of redox-reagent for use in an electrochemical biosensor, the composition comprising a redox enzyme and an electron transfer mediator,
   wherein the electron transfer mediator comprises:
      $Ru(NH_3)_6Cl_3$; and
      thionine, and
   wherein the redox enzyme is flavin adenine dinucleotide-glucose dehydrogenase.

2. The composition as set forth in claim 1, wherein the composition of redox-reagent additionally includes one or more additives selected from the group consisting of surfactant, water-soluble polymer, quarternary ammonium salt, fatty acid and thickener.

3. The composition as set forth in claim 2, wherein the surfactant is selected from the group consisting of Triton X-100, sodium dodecyl sulfate, perfluorooctane sulfonate and sodium stearate.

4. The composition as set forth in claim 2, wherein the water-soluble polymer is selected from the group consisting of polyvinylpyrrolidone, polyvinyl alcohol, polyfluoro sulfonate, hydroxyethyl cellulose, hydroxypropyl cellulose, carboxymethyl cellulose, cellulose acetate, polyamide and a combination thereof.

5. The composition as set forth in claim 2, wherein the quarternary ammonium salt is selected from the group consisting of dodecyltrimethylammonium, ethyltrimethylammonium, myristyl trimethylammonium, cetyltrimethylammonium, octadecyl trimethylammonium, tetrahexylammonium and a combination thereof.

6. The composition as set forth in claim 2, wherein the fatty acid is selected from the group consisting of caproic acid, heptanic acid, caprylic acid, octanoic acid, nonanoic acid, capric acid, undecanoic acid, lauric acid, tridecanoic acid, myristic acid, pentadecanoic acid, palmitic acid, heptadecanoic acid, stearic acid, nonadecanoic acid, arachidonic acid and a combination thereof.

7. The composition as set forth in claim 2, wherein the thickener is diethylaminoethyl-dextran hydrochloride (DEAE-dextran hydrochloride).

8. The composition as set forth in claim 1, wherein the electrochemical biosensor is a glucose biosensor.

9. A planar type electrochemical biosensor comprising:
   a working electrode and a counter electrode provided in one plane; and
   the composition of redox-reagent as set forth in claim 1 coated on the working electrode.

10. A converse type biosensor comprising:
    a working electrode and a counter electrode provided in separate planes and faced with each other; and
    the composition of redox-reagent as set forth in claim 1 coated on the working electrode.

11. The planar type electrochemical biosensor as set forth in claim 9, further comprising:
    a top layer having a channel through which blood is drawn into the electrochemical biosensor;

a bottom layer on which the working electrode and the counter electrode are formed;

a spacer coated with adhesive on both surfaces thereof to attach the top layer and the bottom layer thereto causing the blood to be drawn toward the electrode by capillary action; and an insulating layer having a passage to define areas of the working electrode and the counter electrode.

12. The converse type biosensor as set forth in claim 10, further comprising:

a top layer having a channel through which blood is drawn into the biosensor and on which the counter electrode is printed;

a bottom layer on which the working electrode, a lead of the counter electrode and a flow rate detecting electrode are formed;

a spacer coated with adhesive on both surfaces thereof to attach the top layer and the bottom layer thereto causing the blood to be drawn toward the working, counter, and flow rate detecting electrodes by capillary action;

an insulating layer having a passage to define areas of the working electrode and the counter electrode; and a circuit connect ground to connect the counter electrode to the lead of the counter electrode, wherein, the lead of the counter electrode and the flow rate detecting electrode to measure the velocity of introduced blood, all of which are printed on the bottom layer.

13. A composition of redox-reagent for use in an electrochemical biosensor, the composition comprising a redox enzyme, an electron transfer mediator and a water-soluble polymer, wherein the electron transfer mediator comprises:
    $Ru(NH_3)_6Cl_3$; and
    thionine or 3-amino-7-(2,3,4,5,6-pentahydroxyhexanamido)-5-phenothiazinium, and
wherein the redox enzyme is flavin adenine dinucleotide-glucose dehydrogenase.

14. The composition as set forth in claim 13, wherein the water-soluble polymer is selected from the group consisting of polyvinylpyrrolidone, polyvinyl alcohol, polyfluoro sulfonate, hydroxyethyl cellulose, hydroxypropyl cellulose, carboxymethyl cellulose, cellulose acetate, polyamide, and a combination thereof.

15. A composition of redox-reagent for use in an electrochemical biosensor comprising:

a redox enzyme and an electron transfer mediator,
wherein the electron transfer mediator comprises:
    a ruthenium complex; and
    3-amino-7-(2,3,4,5,6-pentahydroxyhexanamido)-5-phenothiazinium.

16. The composition as set forth in claim 15, wherein the ruthenium complex is selected from the group consisting of $Ru(NH_3)_6Cl_3$, $[Ru(2,2',2''\text{-terpyridine})(1,10\text{-phenanthroline})(OH_2)]^{2+}$, $trans\text{-}[Ru(2,2'\text{-bipyridine})_2(OH_2)(OH)]^{2+}$, $[(2,2'\text{-bipyridine})_2(OH)RuORu(OH)(2,2'bpy)_2]^{4+}$ and $[Ru(4,4'\text{-bipyridine})(NH_3)_5]^{2+}$.

17. The composition as set forth in claim 15, wherein the redox enzyme is selected from the group consisting of flavin adenine dinucleotide-glucose dehydrogenase, nicotinamide adenine dinucleotide-glucose dehydrogenase, glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase and bilirubin oxidase.

18. A planar type electrochemical biosensor comprising:
a working electrode and a counter electrode provided in one plane; and
the composition of redox-reagent as set forth in claim 15 coated on the working electrode.

19. A converse type biosensor comprising:
a working electrode and a counter electrode provided in separate planes and faced with each other; and
the composition of redox-reagent as set forth in claim 15 coated on the working electrode.

* * * * *